US011915517B2

(12) United States Patent
Kawase

(10) Patent No.: US 11,915,517 B2
(45) Date of Patent: *Feb. 27, 2024

(54) IMAGE PROCESSING DEVICE, IMAGE PROCESSING METHOD, FACE RECOGNITION SYSTEM, PROGRAM, AND STORAGE MEDIUM

(71) Applicant: NEC Corporation, Tokyo (JP)

(72) Inventor: Nobuaki Kawase, Tokyo (JP)

(73) Assignee: NEC CORPORATION, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 17/860,639

(22) Filed: Jul. 8, 2022

(65) Prior Publication Data
US 2022/0343677 A1 Oct. 27, 2022

Related U.S. Application Data

(63) Continuation of application No. 16/344,500, filed as application No. PCT/JP2017/030120 on Aug. 23, 2017, now Pat. No. 11,423,693.

(30) Foreign Application Priority Data

Oct. 31, 2016 (JP) ................. 2016-212921

(51) Int. Cl.
*G06V 40/16* (2022.01)
*A61B 5/1171* (2016.01)
(Continued)

(52) U.S. Cl.
CPC .......... *G06V 40/168* (2022.01); *A61B 5/1171* (2016.02); *G06T 1/00* (2013.01);
(Continued)

(58) Field of Classification Search
CPC .. G06V 40/166; G06V 10/145; G06V 40/168; G06V 40/172; G06V 40/45; A61B 5/1171; G06T 1/00; G06T 7/00
See application file for complete search history.

(56) References Cited

U.S. PATENT DOCUMENTS 9,202,105 B1* 12/2015 Wang ............... H04N 21/44008
9,251,427 B1  2/2016 Chu .................... G06K 9/52
(Continued)

FOREIGN PATENT DOCUMENTS

JP  2005-197914 A  7/2005
JP  2006-259931 A  9/2006
(Continued)

OTHER PUBLICATIONS

Joongrock Kim et al., "3D Multi-Spectrum Sensor System with Face Recognition", Sensors, vol. 13, No. 10, Sep. 25, 2013, pp. 12804-12829, (26 pages total).
(Continued)

*Primary Examiner* — Tom Y Lu

(57) ABSTRACT

An example embodiment includes: an acquisition unit that acquires a first image generated by capturing an object by using a light at a first wavelength, a second image generated by capturing the object by using a light at a second wavelength, and depth information on the object; a detection unit that detects a face included in the second image; a check unit that, based on the depth information, checks whether or not a face detected by the detection unit is one obtained by capturing a living body; and an extraction unit that, based on information on a face checked by the check unit as obtained by capturing a living body, extracts a face image from the first image.

23 Claims, 10 Drawing Sheets

(51) Int. Cl.
  *G06T 1/00*     (2006.01)
  *G06T 7/00*     (2017.01)
  *G06V 40/40*    (2022.01)

(52) U.S. Cl.
  CPC .............. *G06T 7/00* (2013.01); *G06V 40/166* (2022.01); *G06V 40/172* (2022.01); *G06V 40/45* (2022.01)

(56) References Cited

U.S. PATENT DOCUMENTS

| | | | |
|---|---|---|---|
| 11,423,693 B2 * | 8/2022 | Kawase | G06V 40/168 |
| 2007/0253604 A1 | 11/2007 | Inoue et al. | |
| 2010/0046807 A1 * | 2/2010 | Sato | G06V 10/141 |
| | | | 250/580 |
| 2013/0015946 A1 | 1/2013 | Lau | G06F 21/32 |
| | | | 340/5.2 |
| 2013/0113956 A1 | 5/2013 | Anderson | G06K 9/00234 |
| | | | 348/223.1 |
| 2014/0049373 A1 | 2/2014 | Spencer | G06K 9/00093 |
| | | | 340/5.83 |
| 2014/0099005 A1 | 4/2014 | Mogi | |
| 2014/0237587 A1 | 8/2014 | Forbes | G06F 21/00 |
| | | | 726/18 |
| 2016/0071275 A1 | 3/2016 | Hirvonen | G06T 7/32 |
| | | | 382/103 |

FOREIGN PATENT DOCUMENTS

| | | | | |
|---|---|---|---|---|
| JP | 2007-004612 A | 1/2007 | | |
| JP | 2007-226549 A | 9/2007 | | |
| JP | 2008-017227 A | 1/2008 | | |
| JP | 2008-158597 A | 7/2008 | | |
| JP | 2008158597 | * | 7/2008 | .............. G06T 1/00 |
| JP | 2008158597 A | 7/2008 | | |
| JP | 2009-211381 A | 9/2009 | | |
| JP | 2013-250856 A | 12/2013 | | |
| JP | 2014-078052 A | 5/2014 | | |
| JP | 2015-528942 A | 10/2015 | | |
| JP | 6428914 B2 | 11/2018 | | |
| WO | 2009/107237 A1 | 9/2009 | | |

OTHER PUBLICATIONS

Saptarshi Chakraborty et al., "An Overview of Face Liveness Detection", International Journal on Information Theory, vol. 3, No. 2, Apr. 30, 2014, pp. 11-25, (16 pages total).

Ivana Chingovska et al., "Face Recognition Systems Under Spoofing Attacks", Face Recognition Across the Imaging Spectrum, Jan. 1, 2016, pp. 165-194, (30 pages total).

Communication dated Oct. 9, 2019, from the European Patent Office in application No. 17864307.8.

Written Opinion of the International Searching Authority dated Nov. 14, 2017 in application No. PCT/JP2017/030120.

International Search Report for PCT Application No. PPCT/JP2017/030120, dated Nov. 14, 2017.

Japanese Office Action for JP Application No. 2021-168012 dated Nov. 1, 2022 with English Translation.

Japanese Office Action dated Jun. 20, 2023 in Japanese Application No. 2021-168012.

* cited by examiner

IMAGE PROCESSING DEVICE, IMAGE PROCESSING METHOD, FACE RECOGNITION SYSTEM, PROGRAM, AND STORAGE MEDIUM

CROSS-REFERENCE TO RELATED APPLICATIONS

The present application is a continuation application of U.S. patent application Ser. No. 16/344,500 filed on Apr. 24, 2019, which is a National Stage Entry of international application PCT/JP2017/030120 filed on Aug. 23, 2017, which claims the benefit of priority from Japanese Patent Application No. 2016-212921 filed on Oct. 31, 2016, the disclosures of all of which are incorporated in their entirety by reference herein.

TECHNICAL FIELD

The present invention relates to an image processing device, an image processing method, a face recognition system, a program, and a storage medium.

BACKGROUND ART

In recent years, in a situation of identity verification, biometrics recognition has been used in which biometrics information that is information on a physical feature or an action feature of a human is used for authentication. Face recognition, which is one type of biometrics recognition, has advantages of less psychological resistance at an authentication object, a capability of performing authentication even from a distant place, a psychological deterrence effect against dishonesty, and the like.

Face recognition is a technology to compare information obtained from a face image of a person captured by a camera with information on a registered person and authenticate whether or not the captured person is the same person as the registered person. Patent Literature 1 and Patent Literature 2 disclose a face recognition scheme using an infrared image as a technology of preventing a so-called impersonate act that is to attempt to pass through face recognition using a non-living body such as a photograph. Since a print such as a photograph has a property that does not absorb infrared light, it is possible to determine whether an object is a living body or a photograph from the captured infrared image and exclude a dishonest act.

CITATION LIST

Patent Literature

PTL 1: International Publication No. WO2009/107237
PTL 2: Japanese Patent Application Laid-Open No. 2008-158597

SUMMARY OF INVENTION

Technical Problem

When a person having a deep colored skin such as a black person is captured by an infrared camera, however, a reflected infrared light cannot be sufficiently detected due to a large absorption rate of the infrared light, and it may be difficult to determine whether or not a living body is captured. Further, when face recognition is performed from an infrared image, the accuracy of face recognition is lower compared to a case where face recognition is performed from a visible light image.

One example object of the present invention is to provide an image processing device, an image processing method, a face recognition system, a program, and a storage medium that can accurately determine a living body and non-living body from a captured image and extract a face image of a living body suitable for face recognition.

Solution to Problem

According to one example aspect of the present invention, provided is an image processing device including: an acquisition unit that acquires a first image generated by capturing an object by using a light at a first wavelength, a second image generated by capturing the object by using a light at a second wavelength, and depth information on the object; a detection unit that detects a face included in the second image; a determination unit that, based on the depth information, determines whether or not a face detected by the detection unit is one obtained by capturing a living body; and an extraction unit that, based on information on a face determined by the determination unit as obtained by capturing a living body, extracts a face image from the first image.

Further, according to another example aspect of the present invention, provided is a face recognition system including: an image processing unit that extracts a face image from a first image generated by capturing an object by using a light at a first wavelength; and a face recognition unit that determines whether or not a person in the face image extracted by the image processing unit is the same as a registered person, and the image processing unit includes an acquisition unit that acquires the first image, a second image generated by capturing the object by using a light at a second wavelength, and depth information on the object, a detection unit that detects a face included in the second image, a determination unit that, based on the depth information, determines whether or not a face detected by the detection unit is one obtained by capturing a living body, and an extraction unit that, based on information on a face determined by the determination unit as obtained by capturing a living body, extracts the face image from the first image.

Further, according to yet another example aspect of the present invention, provided is an image processing method including: acquiring a first image generated by capturing an object by using a light at a first wavelength, a second image generated by capturing the object by using a light at a second wavelength, and depth information on the object; detecting a face included in the acquired second image; based on the depth information, determining whether or not a detected face is one obtained by capturing a living body; and based on information on a face determined as obtained by capturing a living body, extracting a face image from the first image.

Advantageous Effects of Invention

According to the present invention, it is possible to accurately determine a living body and non-living body from a captured image and extract a face image of a living body suitable for face recognition.

DESCRIPTION OF EMBODIMENTS

First Example Embodiment

Figure 1:
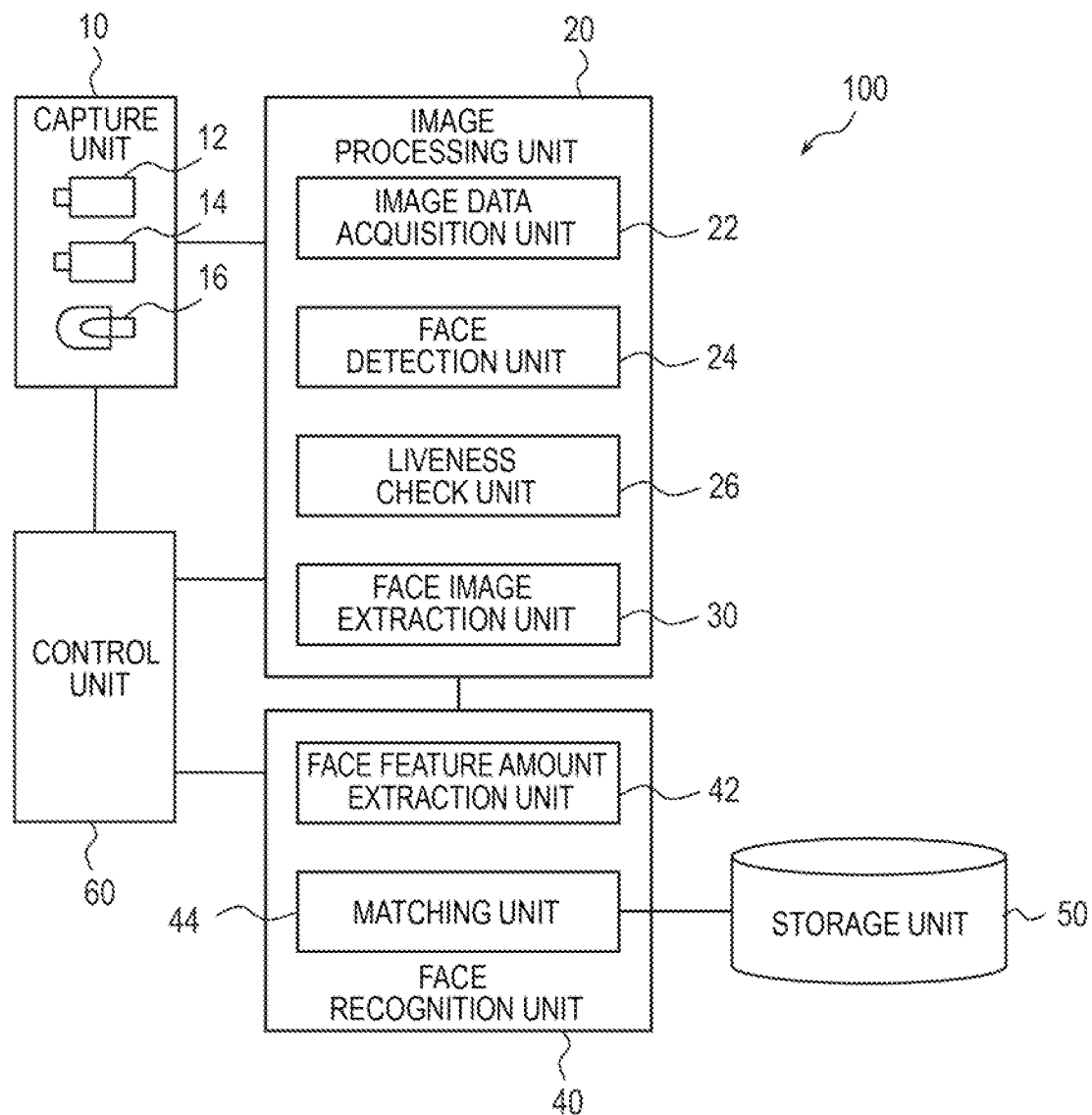
FIG. 1 is a block diagram illustrating a general configuration of a face recognition system according to a first example embodiment of the present invention.

A face recognition system according to a first example embodiment of the present invention will be described with reference to FIG. 1. FIG. 1 is a block diagram illustrating a general configuration of the face recognition system according to the present example embodiment.

As illustrated in FIG. 1, a face recognition system 100 according to the present example embodiment includes a capture unit 10, an image processing unit 20, a face recognition unit 40, a storage unit 50, and a control unit 60.

The capture unit 10 acquires a first image generated by capturing an object by using a light at a first wavelength, a second image generated by capturing the object by using a light at a second wavelength, and depth information (three-dimensional information) of the object. The light at the first wavelength is a visible light, for example. The light at the second wavelength is an infrared light, for example. The capture unit 10 may include a camera 12 that captures a visible light image, a camera 14 that captures a near-infrared image, and a projector 16 that irradiates an object with a laser light of a particular pattern, for example. In the present example embodiment, a case where a visible light image is captured by the camera 12 and a near-infrared image is captured by the camera 14 will be described as an example.

A method of acquiring depth information on an object is not particularly limited. For example, in the example of using the capture unit 10 in the configuration described above, a method of performing capturing by using the camera 14 in a state where a laser light of a particular pattern is irradiated by the projector 16 can be applied. By analyzing a pattern of a reflected light of a laser light of the particular pattern from a captured image, it is possible to measure the distance to an object. Alternatively, a method of measuring the distance to an object based on a parallax of images acquired by a plurality of cameras or a method of measuring the distance to an object by irradiating an object with an infrared laser and using a time difference of a received reflected light (TOF scheme) may be used.

A commercially available product having the same function as the capture unit 10 of the configuration described above may be, for example, Kinect (registered trademark) from Microsoft Corporation, RealSense (registered trademark) from Intel Corporation, or the like. These products have an RGB camera as a unit that captures a visible light image and have a near-infrared projector and a near-infrared camera as a unit that captures an image including depth information on an object.

The image processing unit 20 is a function block that extracts, from images captured by the capture unit 10, a face image in which a living body is captured and includes an image data acquisition unit 22, a face detection unit 24, a liveness check unit 26, and a face image extraction unit 30.

The image data acquisition unit 22 acquires, from the capture unit 10, visible light image data captured by the camera 12, near-infrared image data captured by the camera 14, and depth information on an object. The face detection unit 24 detects a face included in a visible light image and a near-infrared image acquired by the image data acquisition unit 22. The liveness check unit 26 checks whether or not a face image in the near-infrared image detected by the face detection unit 24 is an image obtained by capturing living body based on the depth information on an object acquired by the image data acquisition unit 22. The face image extraction unit 30 extracts a face image used for face recognition from a visible light image based on information on a face included in the near-infrared image.

The face recognition unit 40 is a function block that determines whether or not a person of a face image extracted by the image processing unit 20 matches a pre-registered person and includes a face feature amount extraction unit 42 and a matching unit 44. Note that, while the image processing unit 20 and the face recognition unit 40 are separated here for simplified illustration, the image processing unit 20 may have a function of a part of the face recognition unit 40.

The face feature amount extraction unit 42 extracts, from a face image of a visible light image extracted by the face image extraction unit 30, a face feature amount that is a parameter representing a feature of a face. The matching unit 44 performs a matching process to compare a face feature amount of a face image of the visible light image extracted by the face feature amount extraction unit 42 with a face feature amount of a face image of a person registered in the storage unit 50.

The control unit 60 is a control unit responsible for the entire process in the capture unit 10, the image processing unit 20, and a face recognition unit 40.

Figure 2:
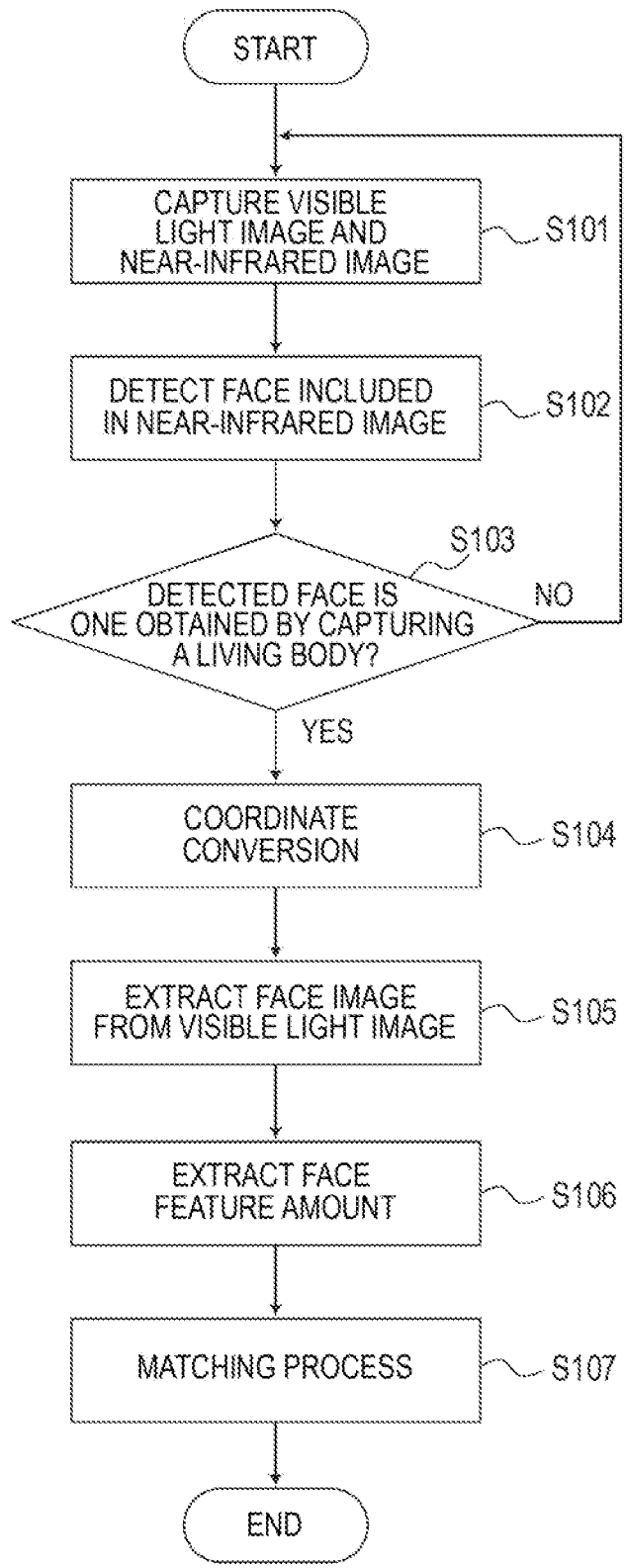
FIG. 2 is a flowchart illustrating a face recognition method in the face recognition system according to the first example embodiment of the present invention.

Next, a face recognition method using the face recognition system 100 according to the present example embodiment will be specifically described by using FIG. 2. FIG. 2 is a flowchart illustrating the face recognition method in the face recognition system according to the present example embodiment.

Some commercially available capture devices in which a visible light camera and a near-infrared camera are integrated have a coordinate conversion function that associates coordinates of an image captured by the visible light camera with coordinates of an image captured by the near-infrared camera. In the present example embodiment, an image processing method using such a coordinate conversion function will be described. Note that a visible light camera and a near-infrared camera formed as separated devices may be used, and a coordinate conversion function that associates coordinates of an image captured by the visible light camera with coordinates of an image captured by the near-infrared camera may be separately prepared.

The face recognition process using the face recognition system 100 according to the present example embodiment is performed in accordance with step S101 to step S107 of FIG. 2. Note that a process of each unit described later is performed under the control by the control unit 60.

First, the capture unit 10 captures an object as a visible light image by using the camera 12 and captures the object as a near-infrared image by using the camera 14. Further, the capture unit 10 acquires depth information on the object by using the camera 14 and the projector 16 (step S101). It is desirable that a visible light image and an infrared image be captured in synchronization. The captured visible light image and the captured near-infrared image are images in which at least the same single person is an object. The depth information on an object is generated by using information on a near-infrared light reflected at the object.

The image data of the visible light image and the image data of the near-infrared image captured by the capture unit 10 are transmitted to the image data acquisition unit 22 of the image processing unit 20 together with the depth information on the object. Note that, in the image data acquisition unit 22, additional image processing such as a correction process may be performed on the received image data, if necessary.

Next, the face detection unit 24 performs a face detection process to detect a face included in an image on the near-infrared image transmitted to the image data acquisition unit 22 (step S102). An algorithm used for face detection by the face detection unit 24 is not particularly limited, and various algorithms can be applied.

Next, the liveness check unit 26 checks whether or not the face image detected from the near-infrared image is an image acquired by the camera 14 capturing a living body (step S103). Specifically, the liveness check unit 26 references the depth information on the object acquired by the capture unit 10 and determines whether or not depth information in accordance with unevenness representing a feature of a living body is included in a face part detected from the near-infrared image.

For example, since a living body includes depth information different for positions in accordance with unevenness of a face, when a distribution of depth information is recognized in a face part, the detected face image can be determined as an image obtained by capturing a living body. On the other hand, since a two-dimensional image such as a photograph does not include depth information that is different for positions in accordance with unevenness of a face, when the depth information on a face part is even, the detected face image can be determined as not obtained by capturing a living body.

In step S103, if it is determined by the liveness check unit 26 that the detected face image is an image obtained by capturing a living body ("YES" in the figure), the process proceeds to step S104. On the other hand, in step S103, if it is determined by the liveness check unit 26 that the detected face image is not an image obtained by capturing a living body ("NO" in the figure), it is determined that face recognition failed, and the process returns to step S101. Note that a case where the detected face is determined as not obtained by capturing a living body includes a case where a face is not detected from the near-infrared image in step S102.

Next, the face image extraction unit 30 uses a coordinate conversion function included in a capture device to convert coordinates on the near-infrared image of the face image determined as obtained by capturing a living body into coordinates on a visible light image (step S104). With a use of the coordinate conversion function provided in the capture device, it is possible to easily determine association to which person's face included in a visible light image the face in the near-infrared image determined as obtained by capturing a living body corresponds.

Next, the face image extraction unit 30 extracts a corresponding face image from the visible light image based on coordinates on the visible light image of the face determined as obtained by capturing a living body (step S105). That is, the face image extraction unit 30 uses information on a face included in the near-infrared image, namely, information on the position of the face included in the near-infrared image in the present example embodiment to extract the face image corresponding to a face included in the near-infrared image from the visible light image. At this time, it is desirable to cut out a slightly wide image taking into consideration of a conversion error from coordinates on the near-infrared image to coordinates on the visible light image.

In such a way, only the face image obtained by capturing a living body can be extracted from a captured visible light image.

Next, the face recognition unit 40 performs a face recognition process by using the face image extracted from the visible light image by the image processing unit 20. By using a visible light image to perform face recognition, it is possible to improve the accuracy of face recognition compared to the case of using a near-infrared image.

First, the face feature amount extraction unit 42 extracts a face feature amount, which is a parameter representing a feature of a face, from the face image extracted in step S105 (step S106). The extraction of a face feature amount may be performed after face detection is performed by the face detection unit 24 on the face image cut out from the visible light image.

The face feature amount is a vector amount, which is a combination of components of scalar amounts each representing a feature of a face image. The component of a feature amount is not particularly limited, and various types of components can be used. For example, as a component of a feature amount, a positional relationship such as a distance or an angle between feature points set at the center or the end point of an organ such as an eye, a nose, a mouth, or the like, a curvature of the outline of a face, a color distribution or a value of light and shade of the surface of a face, or the like can be used. The number of components of the feature amount is not particularly limited and can be suitably set in accordance with a required recognition accuracy, a processing speed, or the like.

Next, the matching unit 44 performs a matching process to match whether or not the person in the face image extracted from the visible light image matches any of the persons registered in the storage unit 50 (step S107). Specifically, the matching unit 44 compares the face feature amount of the face image extracted in step S106 with the face feature amount of the face image of a person registered in the storage unit 50. When a person whose similarity of the face feature amount exceeds a predetermined threshold value exists in the storage unit 50, the matching unit 44 determines that the person of the face image extracted from the visible light image is the same person as a person who is already registered, that is, determines that the face recognition succeeded. On the other hand, when a person whose similarity of the face feature amount exceeds a predetermined threshold value does not exist in the storage unit 50, the matching unit 44 determines that the person of the face image extracted from the visible light image is a person who is not registered in the storage unit 50, that is, determines that the face recognition failed.

The control unit 60 then performs a predetermined process in accordance with a result of the reference process. For example, when the face recognition system of the present example embodiment is used for a gate system of immigration control, access control for a room, or the like, the gate system is controlled so that entry is allowed only when face recognition is successful.

When the similarity of the face feature amount is less than a predetermined threshold value, the face recognition system 100 may determine this as dishonesty and issue an alert. Further, when a detected face is determined as not obtained by capturing a living body despite the fact that the face is detected in the near-infrared image, there is a likelihood that dishonesty to attempt to pass through the gate system by using a photograph or the like is performed. This may be determined as dishonesty, and an alert may be issued in such a case. In contrast, when the storage unit 50 stores a face feature amount of a face image of a person included in a blacklist, the face recognition system 100 may issue an alert when the authentication is successful.

As discussed above, according to the present example embodiment, it is possible to accurately determine a living body and a non-living body from a captured image and extract a face image of a living body suitable for face recognition. Thereby, a face recognition system capable of implementing accurate face recognition can be realized.

Second Example Embodiment

A face recognition system and a face recognition method according to a second example embodiment of the present invention will be described with reference to FIG. 3 to FIG. 5B. The same components as those in the face recognition system according to the first example embodiment are labeled with the same references, and the description thereof will be omitted or simplified.

Figure 3:
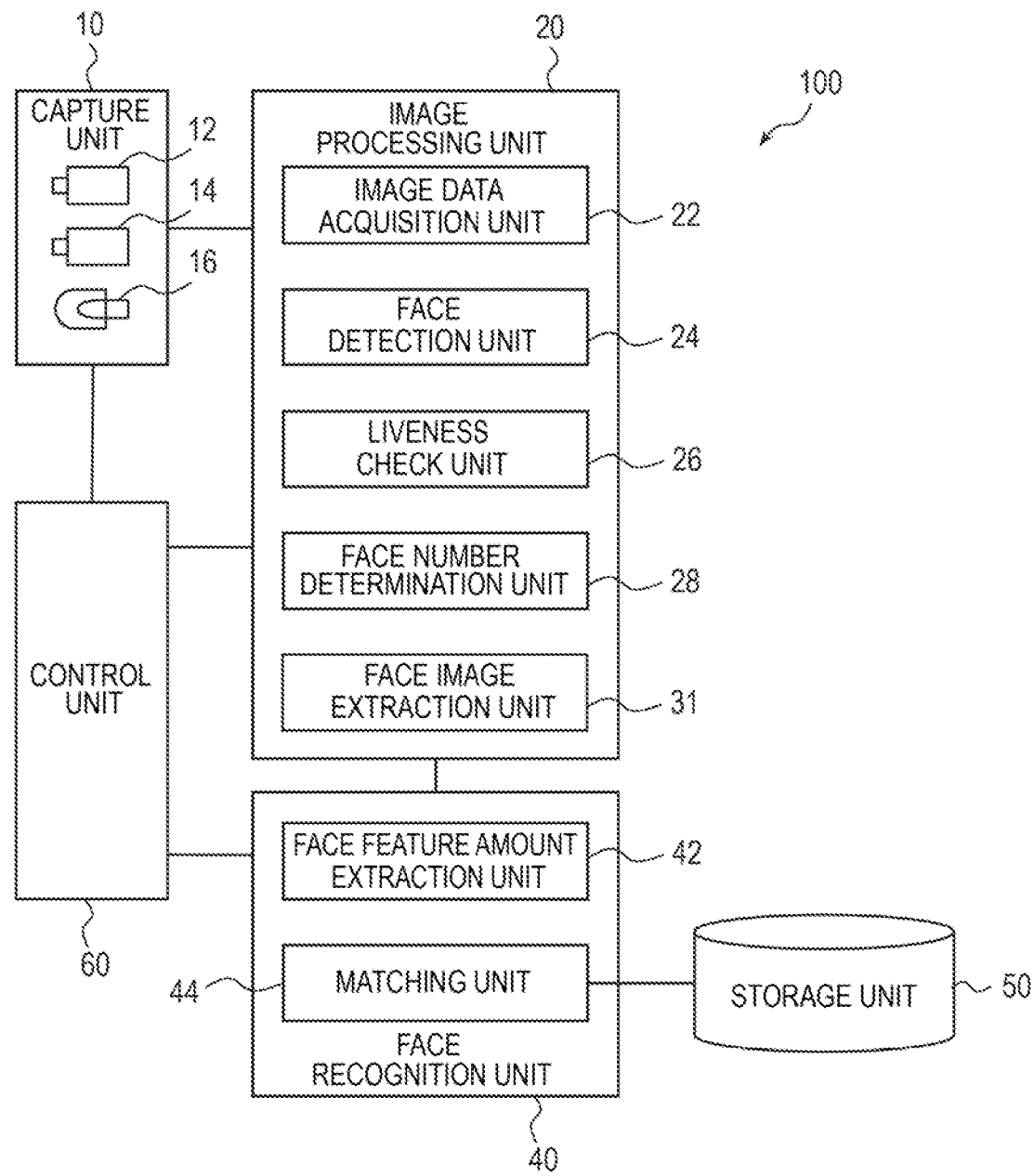
FIG. 3 is a block diagram illustrating a general configuration of a face recognition system according to a second example embodiment of the present invention.

First, a general configuration of the face recognition system according to the present example embodiment will be described by using FIG. 3. FIG. 3 is a block diagram illustrating the general configuration of the face recognition system according to the present example embodiment.

As illustrated in FIG. 3, the face recognition system 100 according to the present example embodiment is the same as the face recognition system according to the first example embodiment illustrated in FIG. 1 except that the image processing unit 20 further includes a face number determination unit 28. The face number determination unit 28 determines the number of faces included in a visible light image and the number of faces determined as obtained by capturing living bodies out of faces included in a near-infrared image.

In the face recognition system of the present example embodiment, association of a visible light image and a near-infrared image is performed based on the number of faces included in the visible light image and the number of faces determined as obtained by capturing living bodies out of faces included in the near-infrared image instead of a coordinate conversion function as used in the first example embodiment. Therefore, the face recognition system of the present example embodiment is not necessarily required to use a capture device having a coordinate conversion function between a visible light image and a near-infrared image.

Figure 4:
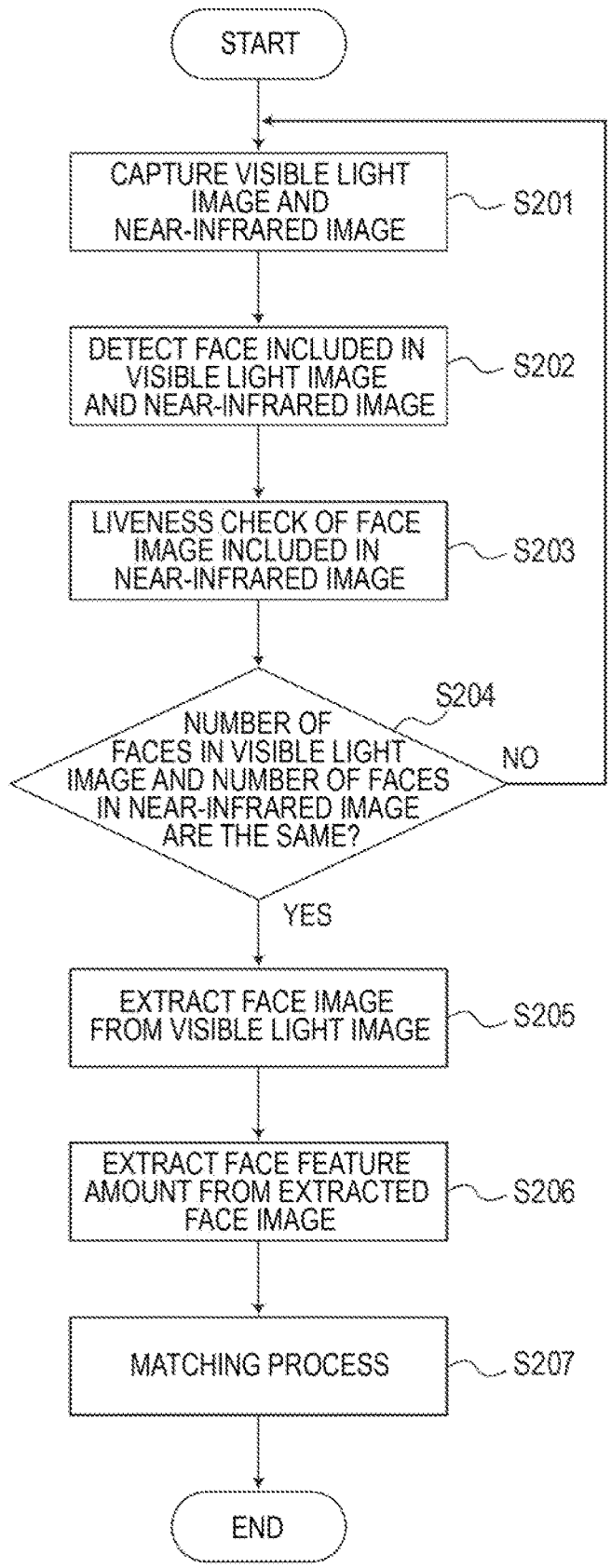
FIG. 4 is a flowchart illustrating a face recognition method in the face recognition system according to the second example embodiment of the present invention.
Figure 5A:
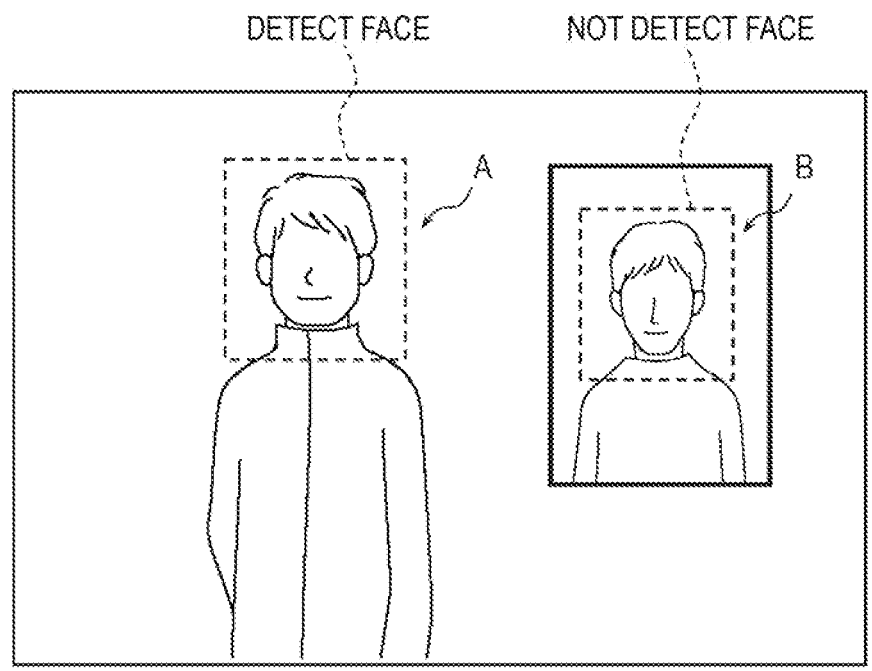
FIG. 5A is a diagram (part 1) illustrating an example of error extraction of a face image when an object including a two-dimensional face image is captured.
Figure 5B:
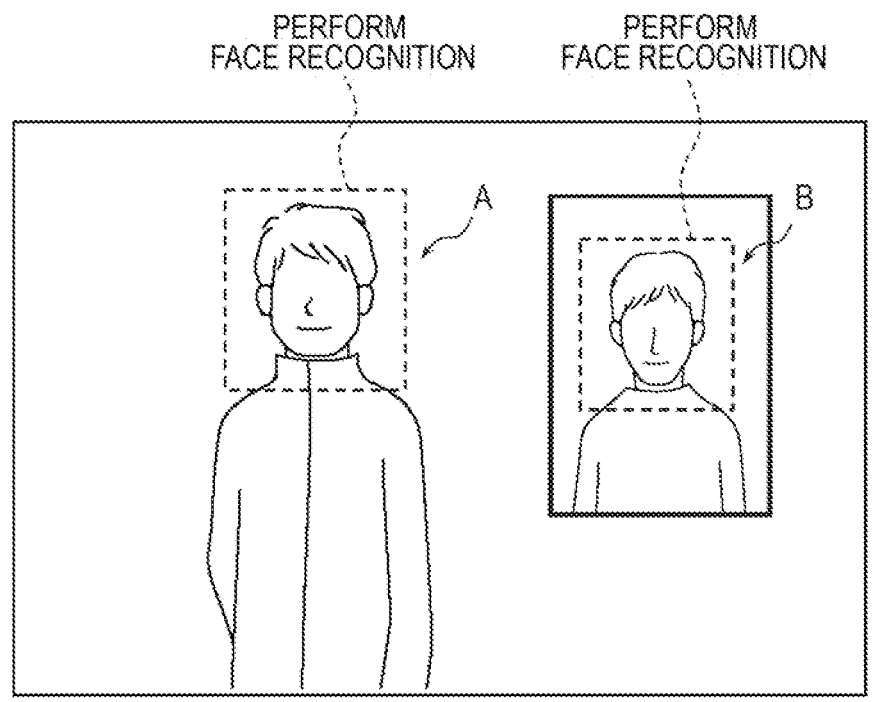
FIG. 5B is a diagram (part 2) illustrating an example of error extraction of a face image when an object including a two-dimensional face image is captured.

Next, the face recognition method using the face recognition system 100 according to the present example embodiment will be specifically described by using FIG. 4 to FIG. 5B. FIG. 4 is a flowchart illustrating the face recognition method in the face recognition system according to the present example embodiment. FIG. 5A and FIG. 5B are diagrams illustrating an example of erroneous extraction of a face image when an object including a two-dimensional face image is captured. FIG. 5A illustrates a near-infrared image, and FIG. 5B illustrates a visible light image.

The face recognition process using the face recognition system 100 according to the present example embodiment is performed in accordance with step S201 to step S207 of FIG. 4. Note that a process of each unit described later is performed under the control by the control unit 60.

First, the capture unit 10 captures an object as a visible light image by using the camera 12 and captures the object as a near-infrared image by using the camera 14. Further, the capture unit 10 acquires depth information on the object by using the camera 14 and the projector 16 (step S201). Since the coordinate conversion function is not used in the present example embodiment, while the camera 12 and the camera 14 may be separate capture devices, it is desirable to perform calibration in advance so that the field of views of the cameras 12 and 14 are substantially the same. The image data of the visible light image and the image data of the near-infrared image captured by the capture unit 10 are transmitted to the image data acquisition unit 22 of the image processing unit 20 together with the depth information on the object.

Next, the face detection unit 24 performs a face detection process to detect a face included in an image on the visible light image and the near-infrared image transmitted to the image data acquisition unit 22, respectively (step S202).

Next, the liveness check unit 26 checks whether or not the face image detected from the near-infrared image is an image acquired by the camera 14 capturing a living body (step S203). If a plurality of faces are detected from the near-infrared image, the liveness check unit 26 checks whether or not each of the face images is an image acquired by capturing a living body. The method of the determination is the same as that in step S103 of the first example embodiment.

Next, the face number determination unit 28 determines the number of faces detected from the visible light image and the number of faces detected from the near-infrared image and determined as obtained by capturing the face of living bodies, and determines whether or not both the numbers are the same (step S204).

If the face number determination unit 28 determines that the numbers of faces are the same in the step S204 ("YES" in the figure), the face number determination unit 28 determines that all the face images detected in the visible light image are images obtained by capturing living bodies, and the process proceeds to step S205. On the other hand, if the face number determination unit 28 determines that the numbers of faces are different from each other in the step S204 ("NO" in the figure), the face number determination unit 28 determines that at least some of the faces detected in the visible light image are images obtained by capturing a two-dimensional image such as a photograph, and the process returns to step S201. In such a case, an alert may be issued indicating the presence of a dishonest act. Furthermore, a face detected from only the visible light image may be identified. Further, the face number determination unit 28 may output a face image of a face detected from only the visible light image as a face obtained by a dishonest act.

Next, the face image extraction unit 31 extracts an image of a face (face image) detected from the visible light image (step S205). This step is performed when the number of faces detected from the visible light image and the number of faces detected from the near-infrared image and determined as obtained by capturing the face of living bodies are the same. That is, in this step, information on a face included in the near-infrared image, namely, the number of faces detected from the near-infrared image and determined as obtained by capturing the face of living bodies in the present example embodiment is used to extract a face image corresponding to a face included in the near-infrared image from the visible light image. Note that, when a face image is extracted from a visible light image, the coordinate conversion function described in the first example embodiment may be used to extract a face image corresponding to a face included in the near-infrared image from the visible light image.

Next, the face feature amount extraction unit 42 extracts a face feature amount, which is a parameter representing a face feature, from the face image extracted from the visible light image in step S205 (step S206). The extraction method of a face feature amount is the same as that in step S106 of the first example embodiment.

Next, the matching unit 44 performs a matching process to match whether or not the person in the face image extracted from the visible light image matches any of the persons registered in the storage unit 50 (step S207). The method of a matching process is the same as that in step S107 of the first example embodiment.

The control unit 60 then performs a predetermined process in accordance with a result of the matching process.

As described above, in the present example embodiment, the detected face image is used as a target of a face recognition process only when the number of faces detected from the visible light image and the number of faces detected from the near-infrared image and determined as obtained by capturing the face of living bodies are the same. The reason for this will be described below.

It is possible to employ an operation in which, when even one image which is determined as not acquired by the camera 14 capturing a living body is present in face images detected from a near-infrared image, it is immediately determined that a dishonest act using a two-dimensional image such as a photograph is performed.

However, for example, when a poster or the like including a human's face is happened to be attached on a wall within a field of view of a camera, a failure such as being unable to enter a face recognition process may occur.

Further, when there is an object which can be detected as a face in a visible light image but is less likely to be detected as a face in a near-infrared image, such as a photograph of a white face, for example, a two-dimensional face image may not be excluded by only the liveness check on the near-infrared image.

For example, as illustrated in FIG. 5A, in a near-infrared image of an object including a person A and a photograph of a person B, it is assumed that the face of the person A has been detected, but the face of the person B has not been detected. In this case, since no liveness check is performed on the face image of the person B, it will be determined that no dishonest act using a two-dimensional image is performed. Then, in a subsequent face recognition process, as illustrated in FIG. 5B, the face of the person A and the face of the person B included in a visible light image are determined to be process targets, and face recognition will be performed thereon, respectively.

As discussed above, when there is an object which is detected as a face in a visible light image but is less likely to be detected as a face in a near-infrared image, the number of faces detected from the visible light image and the number of faces detected from the near-infrared image will be different from each other.

Accordingly, in the present example embodiment, comparison between the number of faces detected in a visible light image and the number of faces detected in a near-infrared image is performed in addition to liveness check on a near-infrared image. When a two-dimensional image that can be detected as a face from a near-infrared image is present in the field of view of a camera, this face image can be excluded by using liveness check. When a two-dimensional image that is unable to be detected as a face from a near-infrared image is present in the field of view of a camera, the presence of this face image can be recognized based on the fact that the number of faces detected in the visible light image and the number of faces detected in the near-infrared image are different from each other. Thereby, a face image to be included in a target of a face recognition process can be appropriately selected out of captured images to perform a face recognition process.

As discussed above, according to the present example embodiment, it is possible to accurately determine a living body and a non-living body from a captured image and extract a face image of a living body suitable for face recognition without converting coordinates of a visible light image into coordinates of a near-infrared image. Thereby, a face recognition system capable of implementing accurate face recognition can be realized.

Third Example Embodiment

A face recognition method according to a third example embodiment of the present invention will be described with reference to FIG. 6 to FIG. 8. The same components as those in the face recognition system according to the first and second example embodiments are labeled with the same references, and the description thereof will be omitted or simplified.

Figure 6:
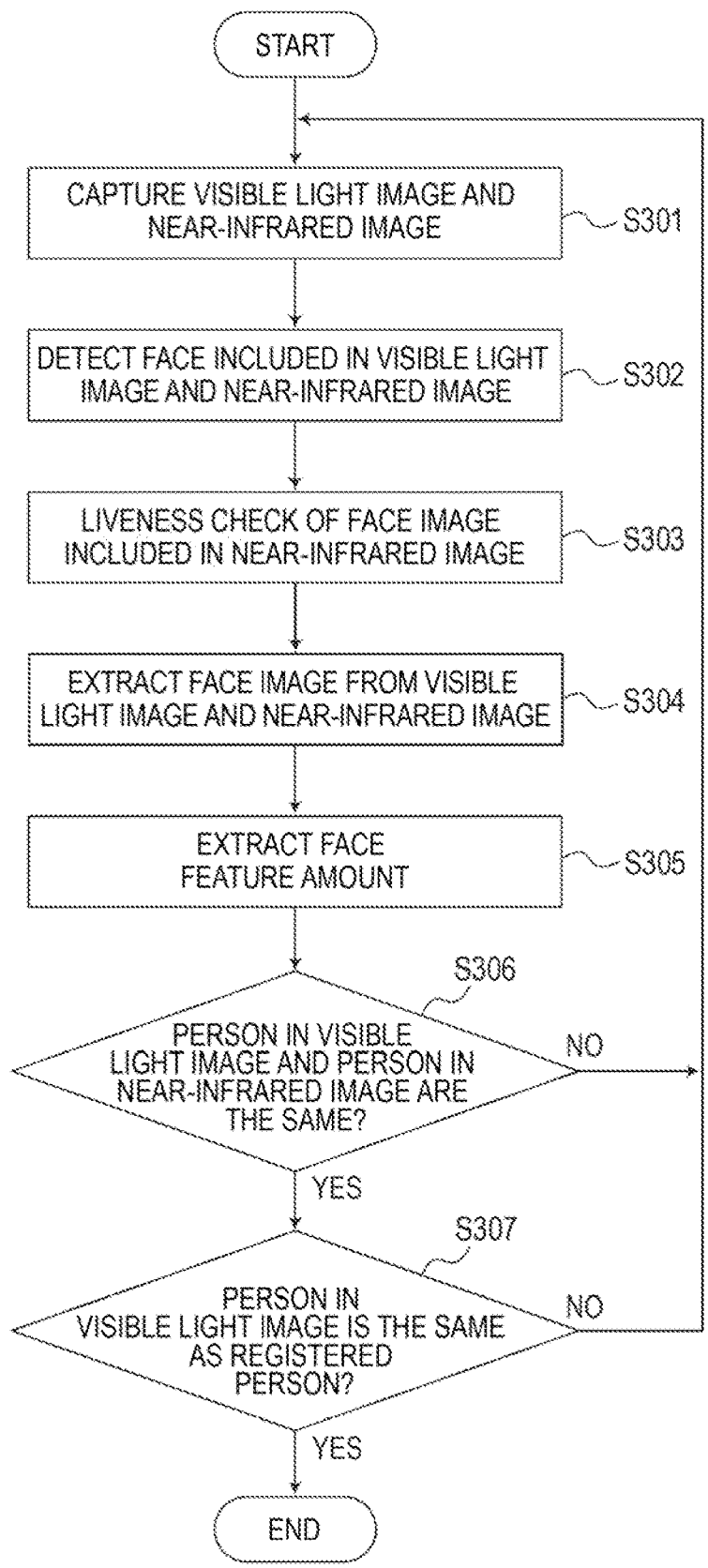
FIG. 6 is a flowchart illustrating a face recognition method in a face recognition system according to a third example embodiment of the present invention.
Figure 7A:
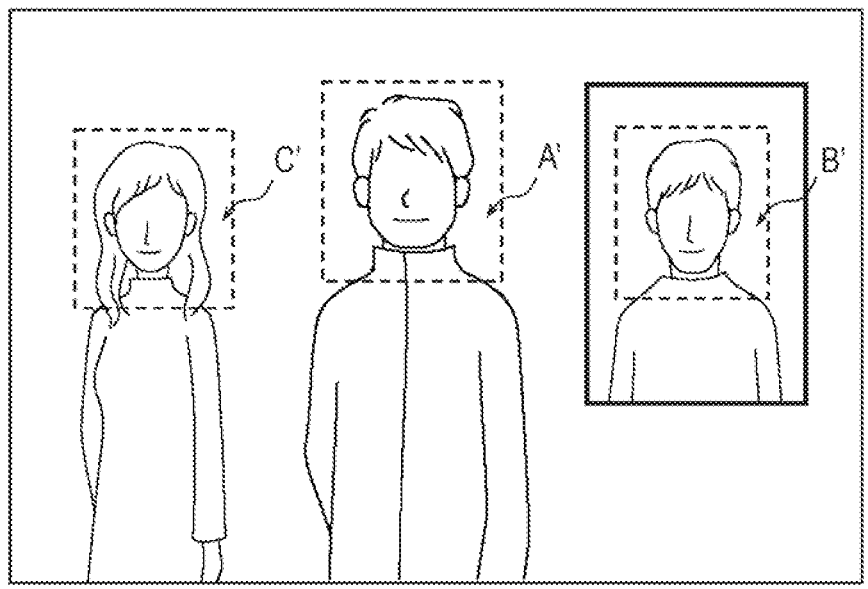
FIG. 7A is a diagram illustrating an example of a visible light image.
Figure 7B:
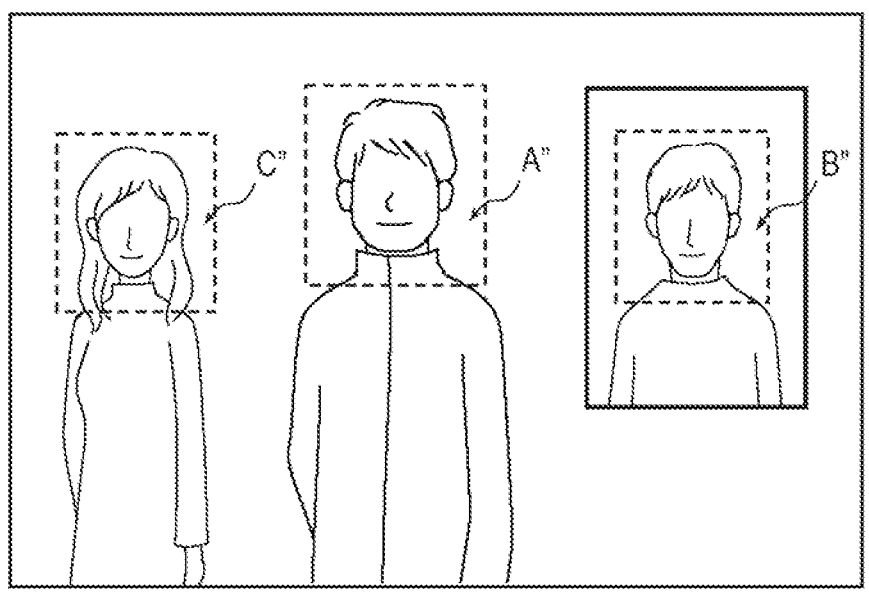
FIG. 7B is a diagram illustrating an example of a near-infrared image.

FIG. 6 is a flowchart illustrating the face recognition method in the face recognition system according to the present example embodiment. FIG. 7A is a diagram illustrating an example of a visible light image captured by the capture unit. FIG. 7B is a diagram illustrating an example of a near-infrared image captured by the capture unit. FIG. 8 is a diagram illustrating an example of face recognition result when a face recognition process of the present example embodiment is performed based on images in FIG. 7A and FIG. 7B.

In the present example embodiment, another face recognition method using the face recognition system according to the first or second example embodiment will be described. The face recognition method of the present example embodiment associates an image captured by the visible light camera with an image captured by a near-infrared camera by using face recognition. Also in the present example embodiment, as with the second example embodiment, the coordinate conversion function used in the first example embodiment may not necessarily be used.

The face recognition process according to the present example embodiment is performed in accordance with step S301 to step S307 of FIG. 6. Note that a process of each unit described later is performed under the control by the control unit 60.

First, the capture unit 10 captures an object as a visible light image by using the camera 12 and captures the object as a near-infrared image by using the camera 14. Further, the capture unit 10 acquires depth information on the object by using the camera 14 and the projector 16 (step S301). The image data of the visible light image and the image data of the near-infrared image captured by the capture unit 10 are transmitted to the image data acquisition unit 22 of the image processing unit 20 together with the depth information on the object.

Next, the face detection unit 24 performs a face detection process to detect a face included in an image on the visible light image and the near-infrared image transmitted to the image data acquisition unit 22, respectively (step S302).

A case where a person A, a person C, and a photograph of a person B are present in the field of views of the cameras 12 and 14 is assumed here as an example. Further, a face of a person A', a face of a person B', and a face of a person C' are detected from a visible light image, for example, as illustrated in FIG. 7A. Further, a face of a person A", a face of a person B", and a face of a person C" are detected from a near-infrared image, for example, as illustrated in FIG. 7B. It is here assumed that the person A and the person B are persons who are already registered in the storage unit 50, and the person C is a person who is not yet registered in the storage unit 50.

Next, the liveness check unit 26 checks whether or not a face detected from the near-infrared image is an image obtained by capturing a living body (step S303). The method of the determination is the same as that in step S103 of the first example embodiment.

In the example of FIG. 7A and FIG. 7B, the face of the person A" and the face of the person C" are determined as images obtained by capturing living bodies, and the face of the person B" is determined as an image obtained by capturing a photograph. Thereby, the face of the person B" is excluded from a group of faces detected from the near-infrared image.

Next, the face image extraction unit 30 extracts an image of a face (face image) detected from the visible light image and a face image determined as detected from the near-infrared image and obtained by capturing a living body (hereafter, referred to as a "biometric face image") (step S304).

Next, the face feature amount extraction unit 42 extracts a face feature amount, which is a parameter representing a feature of a face, from each of the face image detected from the visible light image and the biometric face image detected from the near-infrared image (step S305). The extraction method of a face feature amount is the same as that in step S106 of the first example embodiment.

Next, the matching unit 44 determines whether or not a person of the face image detected from the visible light image is the same as any of persons in the biometric face image detected from the near-infrared image (step S306). Specifically, for all the combinations of the face image detected from the visible light image and the biometric face image detected from the near-infrared image, the matching unit 44 compares the face feature amount of the face image detected from the visible light image with the face feature amount of the biometric face image detected from the near-infrared image. The matching unit 44 then determines a face image to be extracted from the visible light image based on the comparison between the face feature amount of the face image detected from the visible light image and the face feature amount of the biometric face image detected from the near-infrared image. For example, the matching unit 44 determines that the combination in which the similarity between the face feature amounts exceeds a predetermined threshold value is from the same person.

Typically, the number of face images detected from a visible light image is the maximum face detection number. Further, the number of biometric face images detected from a near-infrared image is less than or equal to the maximum face detection number. When the maximum face detection number is N, matching to face images of at most N persons will be performed for a single person. When a plurality of persons whose similarity degree of the face feature amount exceeds a predetermined threshold value are present, a person having the face image of the highest score can be determined as the same person out of the plurality of persons.

If the matching unit 44 determines that at least some of the persons of face images detected from the visible light image match persons of the biometric face image detected from the near-infrared image ("YES" in the figure), the process proceeds to step S307. A face image of the visible light image for which a face image of the same person is not found in the near-infrared image is excluded from a group of the face images detected from the visible light image. In this sense, it can be said that the matching unit 44 is an extraction unit that, out of all the face images of the persons included in the visible light image, extracts one or more face images of the persons included as biometric face images in the near-infrared image.

On the other hand, if the matching unit 44 determines that none of the persons of face images detected from the visible light image matches a person of the biometric face image detected from the near-infrared image ("NO" in the figure), it is determined that the face recognition failed, and the process returns to step S301.

In the example of FIG. 7A and FIG. 7B, it is determined that the face image of the person A' in the visible light image and the face image of the person A" in the near-infrared image are images obtained by capturing the same person A. Further, it is determined that the face image of the person C' in the visible light image and the face image of the person C" in the near-infrared image are images obtained by capturing the same person C. On the other hand, since the face image of the person B" is excluded from the group of face images detected from the near-infrared image, it is determined that a person corresponding to the person B' in the visible light image is not included in the near-infrared image.

Note that the liveness check in step S303 may be performed on and after step S306. In this case, however, since it is necessary to perform a process such as extraction of a face feature amount also on a face image obtained by capturing a two-dimensional image, it is desirable to perform the liveness check before the step S305 in terms of reduction in the processing load.

Next, the matching unit 44 determines whether or not the person of the face image extracted from the visible light image matches any of the persons registered in the storage unit 50 (step S307). Specifically, the matching unit 44 compares a face feature amount of the face image extracted from the visible light image with a face feature amount of the face image of a person registered in the storage unit 50 for each of the face images extracted from the visible light image. If a face image of a person whose similarity of the face feature amount exceeds a predetermined threshold value for each of the face images extracted from the visible light image is present in the storage unit 50, the matching unit 44 determines that the person of the face image extracted from the visible light image is the same as a person who is already registered, that is, determines that the face recognition succeeded. On the other hand, if a face image of a person whose similarity of the face feature amount exceeds a predetermined threshold is not present in the storage unit 50, the matching unit 44 determines that the person of the face image extracted from the visible light image is a person who is not registered in the storage unit 50, that is, determines that the face recognition failed.

If the face recognition is successful in step S307 ("YES" in the drawing), the control unit 60 ends the series of face recognition processes. On the other hand, if the face recognition fails in step S307 ("NO" in the figure), the process returns to step S301.

In the example of FIG. 7A and FIG. 7B, the face image of the person A' in the visible light image is determined as the face image of the person A registered in the storage unit 50, and the face recognition is successful. On the other hand, since the person C is not registered in the storage unit 50, face recognition of the face image of the person C' in the visible light image fails.

Figure 8:
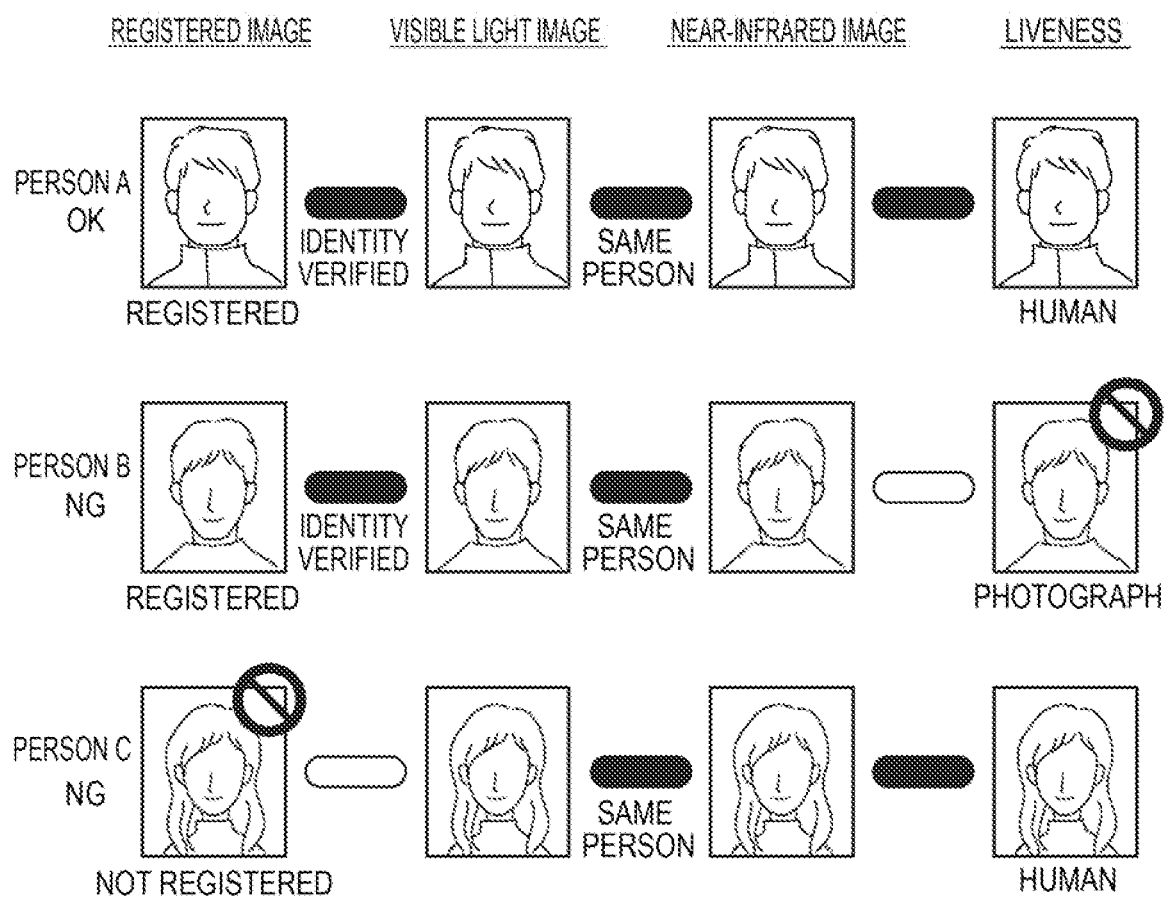
FIG. 8 is a diagram illustrating an example of face recognition result when a face recognition process of the present example embodiment is performed based on images in FIG. 7A and FIG. 7B.

FIG. 8 summarizes a determination result of each step when the face recognition process of the present example embodiment is performed based on the images in FIG. 7A and FIG. 7B.

In the face recognition process of the present example embodiment, face recognition is successful if all the three conditions are satisfied: 1) a person included in a visible light image and a person included in a near-infrared image are the same person, 2) a person in a near-infrared image is an image obtained by capturing a living body, and 3) a person included in a visible light image is a registered person. In FIG. 8, face images which satisfy the condition are connected by black bars, and face images which do not satisfy the condition are connected by white bars. The person A satisfies all the above conditions 1) to 3), and thus face recognition is successful. The person B satisfies the above conditions 1) and 3) but does not satisfy the above condition 2), and thus face recognition fails. The person C satisfies the above conditions 1) and 2) but does not satisfy the above condition 3), and thus face recognition fails.

As described above, the face recognition method according to the present example embodiment realizes matching between an image captured by a visible light camera and an image captured by a near-infrared camera by using face recognition. Therefore, calibration between the visible light camera and the near-infrared camera is unnecessary.

As discussed above, according to the present example embodiment, it is possible to accurately determine a living body and a non-living body from a captured image and extract a face image of a living body suitable for face recognition. Thereby, a face recognition system capable of implementing accurate face recognition can be realized.

Fourth Example Embodiment

A computer device according to a fourth example embodiment of the present invention will be described with reference to FIG. 9. In the present example embodiment, an example of a computer device used for implementing the process of each unit in the face recognition system according to the first to third example embodiments described above will be described.

Figure 9:
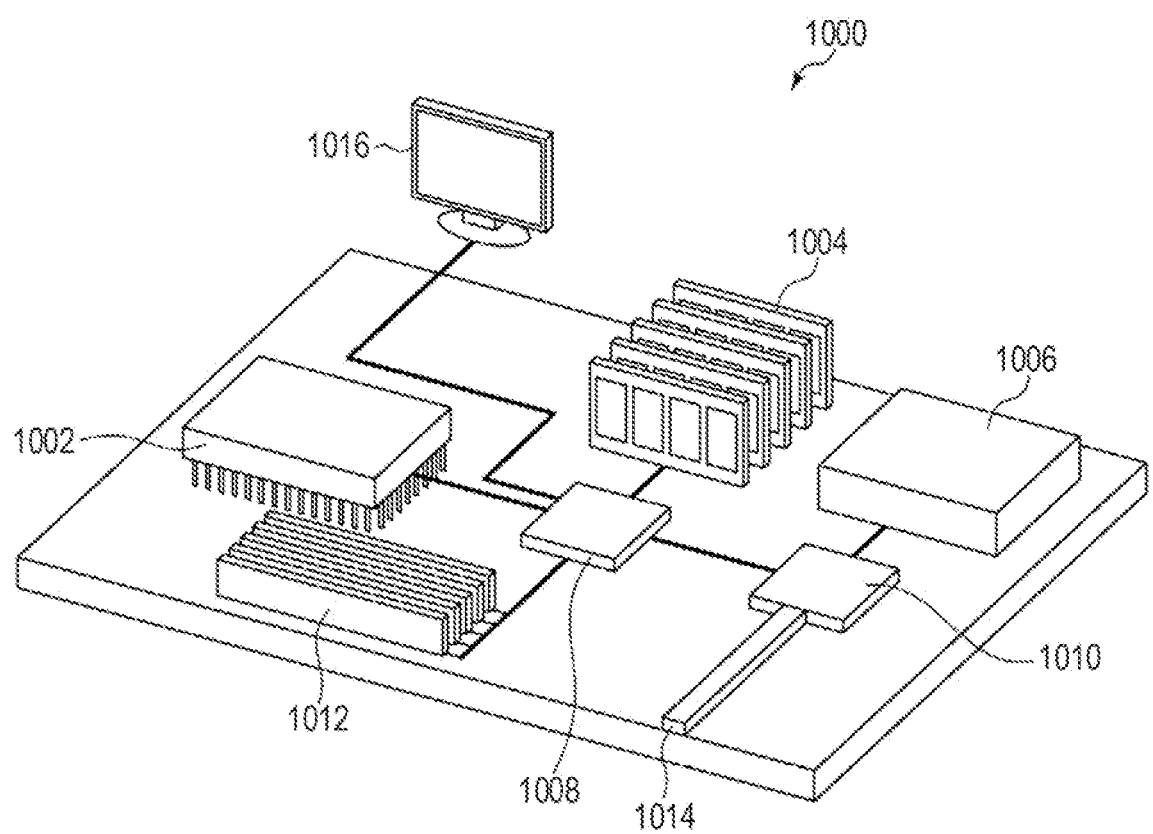
FIG. 9 is a schematic diagram illustrating an example of a computer device.

FIG. 9 illustrates an example of the computer device used for implementing the process of each unit in the face recognition system according to the first to third example embodiments described above. A computer device 1000 illustrated in FIG. 9 is not particularly limited but may be of various types or forms. For example, the computer device 1000 may be a laptop computer, a desktop computer, a workstation, a personal digital assistant, a server, a blade server, a mainframe, an embedded system, or the like.

The computer device 1000 includes a processor 1002, a memory 1004, and a storage device 1006. Further, the computer device 1000 includes a high-speed controller 1008 including a high-speed interface and a low-speed controller 1010 including a low-speed interface. The memory 1004 and a high-speed expansion port 1012 are connected to the high-speed controller 1008. Further, an external input/output device such as a display 1016 or the like is connected to the high-speed controller 1008. On the other hand, a low-speed expansion port 1014 and the storage device 1006 are connected to the low-speed controller 1010.

The processor 1002, the memory 1004, the storage device 1006, the high-speed controller 1008, the low-speed controller 1010, and the high-speed expansion port 1012 are connected to each other through various buses. Further, the processor 1002, the memory 1004, the storage device 1006, the high-speed controller 1008, the low-speed controller 1010, and the high-speed expansion port 1012 may be implemented on a common motherboard or may be implemented in other forms as appropriate.

The processor 1002 is a central processing unit (CPU), for example, and is able to process instructions executed within the computer device 1000. Such instructions include an instruction that is used for displaying graphics information of a graphical user interface (GUI) on an external input/output device such as the display 1016 and stored in the memory 1004 or the storage device 1006.

Further, a plurality of processors, a plurality of busses, or a plurality of processors and a plurality of busses can be used as appropriate together with a plurality of memory devices and multiple types of memory devices. Further, a plurality of computer devices 1000 can be connected to each device that performs a part of the necessary process. For example, a plurality of computer devices 1000 can be connected to each other as a server bank, a group of blade servers, or a multiprocessor system.

The memory 1004 stores therein information within the computer device 1000. For example, the memory 1004 may be a volatile memory unit or a non-volatile memory unit. The memory 1004 may be another computer readable medium, such as a magnetic disk, an optical disk, or the like, for example.

The storage device 1006 can configure mass storage used for the computer device 1000. The storage device 1006 may be a computer readable storage medium such as a floppy (registered trademark) disk device, a hard disk device, an optical disk device, a tape device, a solid-state memory device such as a flash memory, a disk array, or the like or include such a computer readable storage medium, for example. The storage device 1006 may include a storage area network or a device with another configuration. A computer program product may be tangibly embodied in an information carrier. The computer program product can also store an instruction that executes one or a plurality of processes as described above when executed. The information carrier may be a memory device such as the memory 1004, the storage device 1006, or the memory on the processor 1002 or may be a computer readable medium or a machine readable medium such as a carrier signal.

The high-speed controller 1008 manages processes in which the bandwidth for the computer device 1000 is intensively used. On the other hand, the low-speed controller 1010 manages processes in which the bandwidth is less intensively used. However, such allocation of the functions is a mere example, and allocation is not limited thereto. Further, a part or a whole of the high-speed controller 1008 may be incorporated in the processor 1002.

The high-speed controller 1008 is connected to the high-speed expansion port 1012 that can accept the memory 1004 and various expansion cards. Further, the high-speed controller 1008 is connected to the display 1016 via a graphics processor or an accelerator, for example.

Further, the low-speed controller 1010 is connected to the storage device 1006 and the low-speed expansion port 1014. The low-speed expansion port 1014 can include, for example, a communication port of various standards such as Universal Serial Bus (USB), Bluetooth (registered trademark), wired or wireless Ethernet (registered trademark), or the like. One or plurality of input/output devices such as a keyboard, a pointing device, a scanner, or the like can be connected to the low-speed expansion port 1014. Further, one or plurality of network devices such as a switch, a router, or the like can be connected to the low-speed expansion port 1014 via a network adapter, for example.

The computer device 1000 can be implemented in many different forms. For example, the computer device 1000 can be implemented in a form of a typical server or a plurality of servers in a form of a group of such servers. Further, the computer device 1000 can be implemented as a part of the rack server system. Furthermore, the computer device 1000 can be implemented in a form of a personal computer such as a laptop computer, a desktop computer, or the like.

The computer device 1000 can function as at least the image processing unit 20, the face recognition unit 40, and the control unit 60 of the face recognition system 100 according to the first to third example embodiments described above. The processor 1002 controls the entire operation of the computer device 1000 and includes the function of the control unit 60. Further, the processor 1002 can function as the image processing unit 20 by executing the program that implements the function of the image data acquisition unit 22, the face detection unit 24, the liveness check unit 26, the face number determination unit 28, and the face image extraction units 30 and 31. Further, the processor 1002 can function as the face recognition unit 40 by executing the program that implements the function of the face feature amount extraction unit 42 and the matching unit 44.

That is, the processor 1002 executes the program that implements the function of each unit of the image data acquisition unit 22, the face detection unit 24, the liveness check unit 26, the face number determination unit 28, the face image extraction units 30 and 31, the face feature amount extraction unit 42, and the matching unit 44. Thereby, the processor 1002 can function as each unit of the image data acquisition unit 22, the face detection unit 24, the liveness check unit 26, the face number determination unit 28, the face image extraction units 30 and 31, the face feature amount extraction unit 42, and the matching unit 44. Further, the storage device 1006 of the computer device 1000 can function as the storage unit 50.

Note that a part or a whole of the program executed by the processor 1002 of the computer device 1000 can be provided by a computer readable storage medium storing the above, such as a digital versatile disc-read only memory (DVD-ROM), a compact disc-read only memory (CD-ROM), a flash memory such as a USB memory or the like.

Other Example Embodiments

Figure 10:
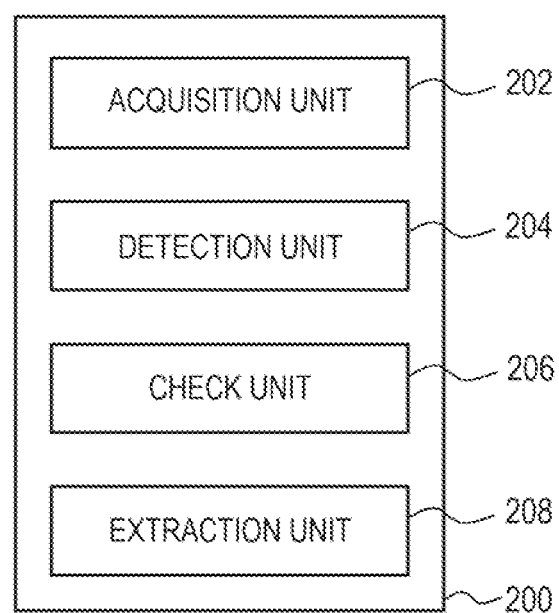
FIG. 10 is a block diagram illustrating a function configuration of an image processing device according to another example embodiment.

The face recognition system described in the first to third example embodiments described above also has a function as an image processing device used for implementing image processing to extract a biometric face image from a visible light image and an image including depth information on an object. The image processing device has the same function as that of the image processing unit 20. That is, according to another example embodiment, the image processing device 200 can be configured as illustrated in FIG. 10. FIG. 10 is a block diagram illustrating a function configuration of the image processing device according to another example embodiment.

As illustrated in FIG. 10, the image processing device 200 includes an acquisition unit 202, a detection unit 204, a check unit 206, and an extraction unit 208. The acquisition unit 202 acquires visible light image data and image data including depth information on an object (for example, near-infrared image data). The detection unit 204 detects a face included in an image acquired by the acquisition unit 202. The check unit 206 checks whether or not a face in the image detected by the detection unit 204 is an image obtained by capturing a living body. The extraction unit 208 extracts a face image used for face recognition from a visible light image based on information on a face included in a near-infrared image. The specific function of each unit is the same as the function of each unit of the image processing unit 20 described in the first to third example embodiments. The image processing device 200 may further have a function as the same determination unit as the face number determination unit 28 included in the image processing unit 20 of the second example embodiment.

Further, the scope of each of the example embodiments includes a processing method that stores, in a storage medium, a program causing the configuration of each of the example embodiments to operate so as to realize the function of each of the example embodiments described above, reads out the program stored in the storage medium as a code, and executes the program in a computer. That is, the scope of each of the example embodiments also includes a computer readable storage medium. Further, each of the example embodiments includes not only the storage medium in which the program described above is stored but also the program itself.

As the storage medium, for example, a floppy (registered trademark) disk, a hard disk, an optical disk, a magneto-optical disk, a CD-ROM, a magnetic tape, a nonvolatile memory card, or a ROM can be used. Further, the scope of each of the example embodiments includes an example that operates on OS to perform a process in cooperation with another software or a function of an add-in board without being limited to an example that performs a process by an individual program stored in the storage medium.

Further, an example in which the configuration of a part of any of the example embodiments is added to another example embodiment or an example in which the configuration of a part of any of the example embodiments is replaced with the configuration of a part of another example embodiment is an example embodiment of the present invention.

Note that all the example embodiments described above are mere embodied examples in implementing the present invention, and the technical scope of the present invention is not to be construed in a limiting sense by these example embodiments. That is, the present invention can be implemented in various forms without departing from the technical concept or the primary feature thereof.

The whole or part of the example embodiments disclosed above can be described as, but not limited to, the following supplementary notes.

(Supplementary Note 1)

An image processing device comprising:
- an acquisition unit that acquires a first image generated by capturing an object by using a light at a first wavelength, a second image generated by capturing the object by using a light at a second wavelength, and depth information on the object;
- a detection unit that detects a face included in the second image;
- a check unit that, based on the depth information, checks whether or not a face detected by the detection unit is one obtained by capturing a living body; and
- an extraction unit that, based on information on a face checked by the check unit as obtained by capturing a living body, extracts a face image from the first image.

(Supplementary Note 2)

The image processing device according to supplementary note 1, wherein the extraction unit extracts a face image corresponding to the face included in the second image from the first image by using information on a position in the second image of a face determined by the check unit as obtained by capturing a living body.

(Supplementary Note 3)

The image processing device according to supplementary note 1 or 2 further comprising a determination unit that determines the number of faces included in an image,
- wherein the detection unit further detects a face included in the first image,
- wherein the determination unit determines the number of faces included in the first image and the number of faces included in the second image based on a detection result from the detection unit, and
- wherein the extraction unit extracts a face image from the first image when the number of faces included in the first image and the number of faces included in the second image are the same.

(Supplementary Note 4)

The image processing device according to any one of supplementary notes 1 to 3, wherein the depth information on the object is information generated by using the light at the second wavelength reflected at the object.

(Supplementary Note 5)

The image processing device according to supplementary note 1 or 2,
- wherein the detection unit further detects a face included in the first image,
- wherein, based on comparison between a face feature amount of the face included in the second image and a face feature amount of the face included in the first image, the extraction unit determines a face image to be extracted from the first image.

(Supplementary Note 6)

The image processing device according to any one of supplementary notes 1 to 5,
- wherein the light at the first wavelength is a visible light, and
- wherein the light at the second wavelength is a near-infrared light.

(Supplementary Note 7)

A face recognition system comprising:
- an image processing unit that extracts a face image from a first image generated by capturing an object by using a light at a first wavelength; and
- a face recognition unit that determines whether or not a person in the face image extracted by the image processing unit is the same as a registered person,
- wherein the image processing unit includes
  - an acquisition unit that acquires the first image, a second image generated by capturing the object by using a light at a second wavelength, and depth information on the object,
  - a detection unit that detects a face included in the second image,
  - a check unit that, based on the depth information, checks whether or not a face detected by the detection unit is one obtained by capturing a living body, and
  - an extraction unit that, based on information on a face checked by the check unit as obtained by capturing a living body, extracts the face image from the first image.

(Supplementary Note 8)

The face recognition system according to supplementary note 7, wherein the extraction unit extracts a face image corresponding to the face included in the second image from the first image by using information on a position in the second image of a face checked by the check unit as obtained by capturing a living body.

(Supplementary Note 9)

The face recognition system according to supplementary note 7 or 8, wherein the image processing unit further includes a determination unit that determines the number of faces included in an image,
- wherein the detection unit further detects a face included in the first image,
- wherein the determination unit determines the number of faces included in the first image and the number of faces included in the second image based on a detection result from the detection unit, and
- wherein the extraction unit extracts a face image from the first image when the number of faces included in the first image and the number of faces included in the second image are the same.

(Supplementary Note 10)

The face recognition system according to any one of supplementary notes 7 to 9, wherein the depth information on the object is information generated by using the light at the second wavelength reflected at the object.

(Supplementary Note 11)

The face recognition system according to supplementary note 9 or 10 further comprising an alert unit that issues an alert indicating dishonesty when the number of faces included in the first image and the number of faces included in the second image are different from each other.

(Supplementary Note 12)

The face recognition system according to supplementary note 7 or 8,
- wherein the detection unit further detects a face included in the first image,
- wherein, based on comparison between a face feature amount of the face included in the second image and a face feature amount of the face included in the first image, the extraction unit determines a face image to be extracted from the first image.

(Supplementary Note 13)

The face recognition system according to any one of supplementary notes 7 to 12, wherein the face recognition unit determines that authentication succeeded when a person of the face image extracted by the extraction unit is the same as a registered person and when a person of the face included in the first image and a person of the face included in the second image are the same person.

(Supplementary Note 14)

The face recognition system according to any one of supplementary notes 7 to 13,
wherein the light at the first wavelength is a visible light, and
wherein the light at the second wavelength is a near-infrared light.

(Supplementary Note 15)

An image processing method comprising:
acquiring a first image generated by capturing an object by using a light at a first wavelength, a second image generated by capturing the object by using a light at a second wavelength, and depth information on the object;
detecting a face included in the acquired second image;
based on the depth information, checking whether or not a detected face is one obtained by capturing a living body; and
based on information on a face checked as obtained by capturing a living body, extracting a face image from the first image.

(Supplementary Note 16)

The image processing method according to supplementary note 15, wherein a face image corresponding to the face included in the second image is extracted from the first image by using information on a position in the second image of a face determined as obtained by capturing a living body.

(Supplementary Note 17)

The image processing method according to supplementary note 15 or 16 further comprising:
detecting further a face included in the acquired first image;
based on a detection result of the face, determining the number of faces included in the first image and the number of faces included in the second image; and
extracting a face image from the first image when the number of faces included in the first image and the number of faces included in the second image are the same.

(Supplementary Note 18)

The image processing method according to any one of supplementary notes 15 to 17, wherein the depth information on the object is information generated by using the light at the second wavelength reflected at the object.

(Supplementary Note 19)

The image processing method according to supplementary note 15 or 16 further comprising:
detecting further a face included in the acquired first image; and
based on a similarity between a face feature amount of the face included in the second image and a face feature amount of the face included in the first image, determining a face image to be extracted from the first image.

(Supplementary Note 20)

The image processing method according to any one of supplementary notes 15 to 19,
wherein the light at the first wavelength is a visible light, and
wherein the light at the second wavelength is a near-infrared light.

(Supplementary Note 21)

A program that causes a computer device to execute steps of: acquiring a first image generated by capturing an object by using a light at a first wavelength, a second image generated by capturing the object by using a light at a second wavelength, and depth information on the object;
detecting a face included in the acquired second image;
based on the depth information, checking whether or not a detected face is one obtained by capturing a living body; and
based on information on a face checked as obtained by capturing a living body, extracting a face image from the first image.

(Supplementary Note 22)

A computer readable storage medium storing the program according to supplementary note 21.

This application is based upon and claims the benefit of priority from Japanese Patent Application No. 2016-212921, filed on Oct. 31, 2016, the disclosure of which is incorporated herein in its entirety by reference.

REFERENCE SIGNS LIST

10 . . . capture unit
20 . . . image processing unit
22 . . . image data acquisition unit
24 . . . face detection unit
26 . . . liveness check unit
28 . . . face number determination unit
30, 31 . . . face image extraction unit
40 . . . face recognition unit
42 . . . face feature amount extraction unit
44 . . . matching unit
50 . . . storage unit
60 . . . control unit
100 . . . face recognition system

The invention claimed is:

1. An image processing device comprising:
a memory configured to store instructions: and
at least one processor configured to execute the instructions to:
acquire a first image generated by capturing an object by using light at a first wavelength, the first image including a face;
acquire a second image generated by capturing the object by using light at a second wavelength, the second image including the face;
acquire three-dimensional information from the second image;
determine, based on the three-dimensional information acquired from the second image, whether or not the face in the second image is one obtained by capturing a living body; and
perform biometric recognition of the object by using the face in the first image and the three-dimensional information acquired from the second image.

2. The image processing device according to claim 1, wherein the processor is further configured to execute the instructions to:
extract a face image corresponding to a face included in the second image from the first image by using information on a position in the second image of the face determined as one obtained by capturing a living body.

3. The image processing device according to claim 1, wherein the processor is further configured to execute the instructions to:

detect a first face included in the first image;
detect a second face included in the second image;
determine the number of faces included in the first image and the number of faces included in the second image based on the detected first face and the detected second face; and
extract a face image from the first image when the number of faces included in the first image and the number of faces included in the second image are the same.

4. The image processing device according to claim 1, wherein the processor is further configured to execute the instructions to:
detect a face included in the first image; and
determine, based on comparison between a face feature amount of a face included in the second image and a face feature amount of the face included in the first image, a face image to be extracted from the first image.

5. The image processing device according to claim 1, wherein the processor is further configured to execute the instruction to determine that a face recognition is successful if the first score and the second score each exceed a predetermined threshold.

6. The image processing device according to claim 1, wherein the processor is further configured to execute the instruction to extract a face feature based on an association of the first image and the second image.

7. The image processing device according to claim 1, wherein the processor is further configured to execute the instruction to issue an alert with the first image if the object is determined to not be a living body based on the second image.

8. The image processing device according to claim 1, wherein the processor is further configured to execute the instructions to:
calculate a first score based on a first face recognition that uses the first image;
calculate a second score based on a second face recognition that uses the second image; and
recognize the object by using at least two scores, including the first score and the second score.

9. A face recognition system comprising:
a memory configured to store instructions: and
at least one processor configured to execute the instructions to:
acquire a first image generated by capturing an object by using light at a first wavelength, the first image including a face;
acquire a second image generated by capturing the object by using light at a second wavelength, the second image including the face;
acquire three-dimensional information from the second image;
determine, based on the three-dimensional information acquired from the second image, whether or not the face in the second image is one obtained by capturing a living body; and
perform biometric recognition of the object by using the face in the first image and the three-dimensional information acquired from the second image.

10. The face recognition system according to claim 9, wherein the processor is further configured to execute the instructions to extract a face image corresponding to a face included in the second image from the first image by using information on a position in the second image of the face determined as one obtained by capturing a living body.

11. The face recognition system according to claim 9, wherein the processor is further configured to execute the instructions to:
detect a first face included in the first image;
detect a second face included in the second image;
determine the number of faces included in the first image and the number of faces included in the second image based on the detected first face and the detected second face; and
extract a face image from the first image when the number of faces included in the first image and the number of faces included in the second image are the same.

12. The face recognition system according to claim 11, wherein the processor is further configured to issue an alert indicating dishonesty when the number of faces included in the first image and the number of faces included in the second image are different from each other.

13. The face recognition system according to claim 9, wherein the processor is further configured to execute the instructions to:
detect a face included in the first image, and
determine, based on comparison between a face feature amount of a face included in the second image and a face feature amount of the face included in the first image, a face image to be extracted from the first image.

14. The face recognition system according to claim 9, wherein the processor is further configured to execute the instructions to determine that authentication succeeded when a person of an extracted face image is the same as a registered person and when a person of a face included in the first image and a person of a face included in the second image are the same person.

15. The face recognition system according to claim 9, wherein the processor is further configured to execute the instruction to determine that a face recognition is successful if the first score and the second score each exceed a predetermined threshold.

16. The face recognition system according to claim 9, wherein the processor is further configured to execute the instruction to extract a face feature based on an association of the first image and the second image.

17. The face recognition system according to claim 9, wherein the processor is further configured to execute the instruction to issue an alert with the first image if the object is determined to not be a living body based on the second image.

18. The face recognition system according to claim 9, wherein the processor is further configured to execute the instructions to:
calculate a first score based on a first face recognition that uses the first image;
calculate a second score based on a second face recognition that uses the second image; and
recognize the object by using at least two scores, including the first score and the second score.

19. An image processing method comprising:
acquiring acquire a first image generated by capturing an object by using light at a first wavelength, the first image including a face;
acquiring a second image generated by capturing the object by using light at a second wavelength, the second image including the face;
acquiring three-dimensional information from the second image;

determining, based on the three-dimensional information acquired from the second image, whether or not the face in the second image is one obtained by capturing a living body; and performing biometric recognition of the object by using the face in the first image and the three-dimensional information acquired from the second image.

20. The image processing method according to claim 19, wherein a face image corresponding to a face included in the second image is extracted from the first image by using information on a position in the second image of the face determined as one obtained by capturing a living body.

21. The image processing method according to claim 19 further comprising:

detecting a first face included in the first image;

detecting a second face included in the second image;

determining the number of faces included in the first image and the number of faces included in the second image based on the detected first face and the detected second face; and extracting a face image from the first image when the number of faces included in the first image and the number of faces included in the second image are the same.

22. The image processing method according to claim 19 further comprising:

detecting a face included in the acquired first image; and based on a similarity between a face feature amount of a face included in the second image and a face feature amount of the face included in the first image, determining a face image to be extracted from the first image.

23. The image processing method according to claim 19 further comprising:

calculating a first score based on a first face recognition that uses the first image;

calculating a second score based on a second face recognition that uses the second image; and recognizing the object by using at least two scores, including the first score and the second score.

* * * * *